United States Patent
Kulas et al.

(10) Patent No.: US 9,883,873 B2
(45) Date of Patent: Feb. 6, 2018

(54) SURGICAL BURS WITH GEOMETRIES HAVING NON-DRIFTING AND SOFT TISSUE PROTECTIVE CHARACTERISTICS

(71) Applicant: Medtronic PS Medical, Inc., Fort Worth, TX (US)

(72) Inventors: John W. Kulas, Euless, TX (US); Donald E. Stearns, Fort Worth, TX (US)

(73) Assignee: Medtronic PS Medical, Inc., Louisville, CO (US)

( * ) Notice: Subject to any disclaimer, the term of this patent is extended or adjusted under 35 U.S.C. 154(b) by 3 days.

(21) Appl. No.: 13/944,650

(22) Filed: Jul. 17, 2013

(65) Prior Publication Data
US 2015/0025559 A1 Jan. 22, 2015

(51) Int. Cl.
*A61B 17/16* (2006.01)
*B23C 5/10* (2006.01)
*A61C 3/02* (2006.01)

(52) U.S. Cl.
CPC ...... *A61B 17/1695* (2013.01); *A61B 17/1615* (2013.01); *B23C 5/1009* (2013.01); *A61C 3/02* (2013.01); *B23C 2210/0407* (2013.01)

(58) Field of Classification Search
CPC . A61B 17/16; A61B 17/1695; A61B 17/1615; A61B 17/1642; A61B 17/1617; B23C 5/02; B23C 5/1009; A61C 1/084; A61C 1/082; A61C 1/085; A61C 1/186; A61C 3/02; A61C 5/40
USPC ............ 606/79–80, 180, 102, 107, 187, 83; 408/109, 202, 227, 230, 147; 433/72, 75, 433/102, 134, 143, 144
See application file for complete search history.

(56) References Cited

U.S. PATENT DOCUMENTS

| 180,554 | A | 8/1876 | Cubberley |
| 372,400 | A | 11/1887 | Browne |
| 533,573 | A | 2/1895 | Wilkens |
| 1,309,706 | A | 7/1919 | Taylor |
| 2,847,885 | A | 8/1956 | Wagner |

(Continued)

FOREIGN PATENT DOCUMENTS

| CN | 101745679 | 6/2010 |
| CN | 201565651 | 9/2010 |

(Continued)

OTHER PUBLICATIONS

End Mill and Cutting Tool Design Criteria and Technical Features. Melin Tool Company. Retrieved from http://www.endmill.com/pages/training/design.html on Jun. 14, 2013. (pp. 1-4).

(Continued)

*Primary Examiner* — Tatiana Nobrega
*Assistant Examiner* — Marcela I. Shirsat
(74) *Attorney, Agent, or Firm* — Harness Dickey (57) ABSTRACT

A surgical bur includes a body and a drill point. The body includes flutes and lands. Each of the flutes includes a cutting edge, a rake face, and a clearance surface. Each of the lands is convex-shaped and disposed between a pair of the flutes. The drill point includes axial relief surfaces. Each of the axial relief surfaces has a planar area, is distinct from the lands and borders (i) a distal portion of one of the cutting edges, (ii) one of the lands, and (iii) one of the clearance surfaces.

43 Claims, 8 Drawing Sheets

(56) References Cited

U.S. PATENT DOCUMENTS

| | | |
|---|---|---|
| 2,795,979 A | 6/1957 | Zerwick |
| 2,847,895 A | 8/1958 | Wagner |
| 2,903,922 A | 9/1959 | Ernst |
| 3,387,511 A | 6/1968 | Ackart, Sr. |
| 3,872,594 A | 3/1975 | Gerteisen |
| 3,937,222 A | 2/1976 | Banko |
| 4,445,509 A | 5/1984 | Auth |
| 4,594,034 A | 6/1986 | Maier |
| 4,600,006 A | 7/1986 | Baker |
| 4,602,900 A | 7/1986 | Arpaio, Jr. et al. |
| 4,699,550 A | 10/1987 | Baker |
| 4,740,121 A | 4/1988 | Arnold |
| 4,803,982 A | 2/1989 | Baker |
| 4,830,000 A | 5/1989 | Shutt |
| 4,951,690 A | 8/1990 | Baker |
| 4,975,003 A | 12/1990 | Hosoi |
| 4,978,350 A | 12/1990 | Wagenknecht |
| 5,007,911 A | 4/1991 | Baker |
| 5,011,342 A * | 4/1991 | Hsu .............................. 408/224 |
| 5,122,134 A | 6/1992 | Borzone et al. |
| 5,143,490 A | 9/1992 | Kopras |
| 5,190,548 A | 3/1993 | Davis |
| 5,209,612 A | 5/1993 | Kish |
| 5,236,291 A | 8/1993 | Agapiou et al. |
| 5,302,059 A | 4/1994 | Fabiano |
| 5,429,504 A | 7/1995 | Peltier et al. |
| 5,467,837 A | 11/1995 | Miller et al. |
| 5,514,141 A | 5/1996 | Prizzi, Jr. |
| 5,575,650 A | 11/1996 | Niznick et al. |
| 5,579,185 A | 11/1996 | Tsai et al. |
| D378,780 S | 4/1997 | Shuler |
| 5,618,293 A | 4/1997 | Sample et al. |
| 5,658,305 A | 8/1997 | Baker |
| 5,810,517 A | 9/1998 | Bostic |
| 5,833,402 A | 11/1998 | Martin |
| 5,846,035 A | 12/1998 | Karafillis et al. |
| 5,855,581 A | 1/1999 | Koblish et al. |
| 5,913,867 A | 6/1999 | Dion |
| 5,964,553 A * | 10/1999 | Blomberg et al. ............. 408/224 |
| 5,980,525 A | 11/1999 | Bryant et al. |
| 6,068,632 A | 5/2000 | Carchidi et al. |
| 6,132,448 A | 10/2000 | Perez et al. |
| 6,238,398 B1 | 5/2001 | Lechot |
| 6,258,093 B1 | 7/2001 | Edwards et al. |
| 6,332,886 B1 | 12/2001 | Green et al. |
| 6,431,801 B2 | 8/2002 | Vasudeva et al. |
| 6,435,780 B1 | 8/2002 | Flynn |
| 6,511,493 B1 | 1/2003 | Moutafis et al. |
| 6,514,258 B1 | 2/2003 | Brown et al. |
| 6,547,495 B2 | 4/2003 | Meece et al. |
| 6,562,046 B2 | 5/2003 | Sasso |
| 6,579,298 B1 | 6/2003 | Bruneau et al. |
| 6,682,349 B1 * | 1/2004 | Logeart ................... A61C 3/02 408/226 |
| 6,783,533 B2 | 8/2004 | Green et al. |
| 7,520,703 B2 | 4/2009 | Rompel |
| 7,862,263 B2 | 1/2011 | van Iperen |
| 8,414,228 B2 | 4/2013 | Wells et al. |
| 8,460,298 B2 | 6/2013 | O'Donoghue |
| 2003/0097133 A1 | 5/2003 | Green et al. |
| 2004/0057803 A1 | 3/2004 | Walrath |
| 2005/0203526 A1 | 9/2005 | Ellis |
| 2005/0272004 A1 | 12/2005 | Desrosiers |
| 2005/0273107 A1 | 12/2005 | Stevens |
| 2005/0283160 A1 | 12/2005 | Knisely et al. |
| 2006/0045639 A1 | 3/2006 | Flynn et al. |
| 2006/0067797 A1 | 3/2006 | Calamia |
| 2006/0085005 A1 | 4/2006 | Kenealy et al. |
| 2006/0142775 A1 | 6/2006 | Heneberry et al. |
| 2007/0010822 A1 | 1/2007 | Zalenski et al. |
| 2007/0160437 A1 | 7/2007 | Shultz et al. |
| 2007/0163416 A1 | 7/2007 | Burgess |
| 2007/0213736 A1 | 9/2007 | Ducharme |
| 2007/0280792 A1 | 12/2007 | Kochan et al. |
| 2007/0298376 A1 | 12/2007 | Kmiecz et al. |
| 2008/0132929 A1 | 6/2008 | O'Sullivan et al. |
| 2008/0140078 A1 * | 6/2008 | Nelson ............... A61B 17/1615 606/80 |
| 2008/0167653 A1 | 7/2008 | Watlington et al. |
| 2008/0177294 A1 | 7/2008 | O'Neil et al. |
| 2008/0193234 A1 | 8/2008 | Davancens et al. |
| 2008/0215148 A1 | 9/2008 | Lesinski et al. |
| 2009/0023988 A1 | 1/2009 | Korner et al. |
| 2009/0024129 A1 | 1/2009 | Gordon et al. |
| 2009/0048602 A1 | 2/2009 | O'Donoghue |
| 2009/0138015 A1 | 5/2009 | Conner et al. |
| 2009/0216235 A1 | 8/2009 | Ellis |
| 2009/0222009 A1 | 9/2009 | Ellis |
| 2009/0264888 A1 | 10/2009 | Neumeyer et al. |
| 2010/0054884 A1 | 3/2010 | Masuda et al. |
| 2010/0057087 A1 | 3/2010 | Cha |
| 2010/0121365 A1 | 5/2010 | O'Sullivan et al. |
| 2010/0145341 A1 | 6/2010 | Ranck et al. |
| 2010/0178631 A1 | 7/2010 | Gordils Wallis et al. |
| 2010/0209200 A1 | 8/2010 | Delacretaz |
| 2010/0286695 A1 | 11/2010 | Hannani et al. |
| 2011/0015634 A1 | 1/2011 | Smith et al. |
| 2011/0054884 A1 | 3/2011 | Drakwall et al. |
| 2011/0098710 A1 | 4/2011 | Spratt et al. |
| 2011/0112540 A1 | 5/2011 | McLean et al. |
| 2011/0208194 A1 | 8/2011 | Steiner et al. |
| 2011/0211922 A1 | 9/2011 | Maeda et al. |
| 2011/0238070 A1 | 9/2011 | Santangelo et al. |
| 2011/0238099 A1 | 9/2011 | Loreth |
| 2012/0150209 A1 | 6/2012 | Gubellini et al. |
| 2012/0158028 A1 | 6/2012 | O'Sullivan et al. |
| 2012/0330315 A1 | 12/2012 | Ranck et al. |
| 2013/0028677 A1 | 1/2013 | Schwaegert et al. |
| 2013/0051937 A1 | 2/2013 | Volokh et al. |
| 2013/0274779 A1 | 10/2013 | Kulas et al. |
| 2014/0058423 A1 | 2/2014 | Smith et al. |
| 2015/0297243 A1 | 10/2015 | Kulas et al. |

FOREIGN PATENT DOCUMENTS

| | | |
|---|---|---|
| DE | 19826276 C1 | 11/1999 |
| EP | 1872739 A1 | 1/2008 |
| JP | H06155126 A | 6/1994 |
| JP | 10-263914 | 10/1998 |
| JP | H10-263914 A | 10/1998 |
| JP | 2003291024 A | 10/2003 |
| JP | 2010-510042 A | 4/2010 |
| WO | WO-2007010389 A1 | 1/2007 |
| WO | WO-2008061711 A2 | 5/2008 |
| WO | WO-2008064350 A2 | 5/2008 |
| WO | WO-2010061933 A1 | 6/2010 |
| WO | WO-2011023381 A1 | 3/2011 |
| WO | WO-2011132876 A2 | 10/2011 |
| WO | WO-2012083468 A1 | 6/2012 |
| WO | WO-2014037518 A1 | 3/2014 |
| WO | WO-2015160884 A1 | 10/2015 |

OTHER PUBLICATIONS

International Search Report and Written Opinion dated Oct. 10, 2014 for PCT/US2014/046827 claiming benefit of U.S. Appl. No. 13/944,650 filed Jul. 17, 2013.

Find Your Perfect Balance. Midas Rex Legend 7.5. cm Attachments and Tools. Medtronic brochure. (2012) 3 pages.

Table of Contents, RedLine Tools catalog, www.redlinetools.com/Images/PDFs/Redline09/RL062009_Sec1_Front%20pl-9_72.pdf, pp. 1-8.

Innovations 2005 catalog, Komet GEBR. BRASSELER GmbH & Co., KG, Lemgo, Germany, 28 pages.

Komet Burs mini catalogue 2007, Henry Schein Halas, www.henryschein.com.au, 19 pages.

Komet Surgery catalog, Mar. 2011, 8 pages.

Stryker Neuro Spine ENT brochure, Zyphr Burs, Kalamazoo, Michigan, www.stryker.com, 2011, 6 pages.

International Search Report and Written Opinion dated Aug. 28, 2013 for PCT/US2013/036269, claiming priority to U.S. Appl. No. 13/447,372, filed Apr. 16, 2012.

(56) References Cited

OTHER PUBLICATIONS

International Preliminary Report on Patentability and Written Opinion dated Oct. 21, 2014 for PCT/US2013/036269, claiming priority to U.S. Appl. No. 13/447,372, filed Apr. 16, 2012.
International Preliminary Report on Patentability and Written Opinion mailed Jan. 19, 2016 for PCT/US2014/046827, claiming priority to U.S. Appl. No. 13/944,650, filed Jul. 17, 2013.
U.S. Appl. No. 14/664,258, 2015-0297243, filed Mar. 20, 2015, Kulas.
U.S. Appl. No. 14/664,002, filed Mar. 31, 2015, Kulas.
U.S. Appl. No. 14/840,217, filed Aug. 31, 2015, Vu.
U.S. Appl. No. 14/992,400, 2016-0120552, filed Jan. 11, 2016, Kulas.
Canadian Office Action dated Sep. 29, 2015 for Canadian Application 2,870,689 claiming benefit of International Application PCT/US2013/036269 claiming benefit of U.S. Appl. No. 13/447,372, filed Apr. 16, 2012.
Chinese Office Action (English translation) dated May 24, 2016 for Chinese Application No. 2013800311659 which claims benefit of PCT/2013/036269 filed Apr. 12, 2013.
International Search Report and Written Opinion dated Jul. 25, 2016 for PCT/US2016/023349 which claims benefit the benefit of U.S. Appl. No. 14/674,002, filed Mar. 31, 2015.
Japanese Office Action dated Nov. 10, 2015 for Japanese Application No. 2015-507064 claiming benefit of PCT/US2014/046827 claiming benefit of U.S. Appl. No. 13/944,650 filed Jul. 17, 2013.
Japanese Office Action dated Jun. 21, 2016 for Japanese Application No. 2015-50764 claiming benefit of PCT/US2013/036269 claiming benefit of U.S. Appl. No. 13/447,372 filed Apr. 12, 2013 with English translation.
Canadian Office Action dated Aug. 4, 2016 for CA Application No. 2870689 for PCT/US2013/036269 which claims benefit of U.S. Appl. No. 13/447,372, filed Apr. 16, 2012.
Korean Office Action dated Mar. 16, 2016 for KR Application No. 10-2014-7031869 for PCT/US2013/036269 which claims benefit of U.S. Appl. No. 13/447,372, filed Apr. 16, 2012 with English translation.
Australian Office Action dated Jun. 23, 2015 for AU Application No. 2013249626 for PCT/US2013/036269 which claims benefit of U.S. Appl. No. 13/447,372, filed Apr. 16, 2012.
Korean Office Action dated Sep. 30, 2016 for Korean Application No. 10-2014-7031869 corresponding to PCT/US2013/036269 which claims benefit of U.S. Appl. No. 13/447,372, filed Apr. 16, 2012 with English translation.
Australian Office Action dated Mar. 15, 2017 for AU Application No. 2015247768.
Canadian Office Action dated Sep. 29, 2015 for Canadian Application No. 2,870,689 claiming benefit of PCT/US2013/036269.
Canadian Office Action dated May 1, 2017 for CA Application No. 2,917,601.
Chinese Office Action (English translation) dated May 24, 2016 for Chinese Application No. 2013800311669 which claims benefit of PCT/2013/036269 filed Apr. 12, 2013.
International Search Report and Written Opinion dated Jul. 25, 2016 for Application No. PCT/US2014/046827 which claims benefit of U.S. Appl. No. 13/944,650, filed Jul. 17, 2013.
Japanese Office Action dated Nov. 10, 2015 for Japanese Application No. 2015-507064 claiming benefit of PCT/US2014/046827 claiming benefit of U.S. Appl. No. 13/944,650, filed Jul. 17, 2013.
Japanese Office Action dated Jun. 21, 2016 for Japanese Application No. 2015-50764 claiming benefit of PCT/US2013/036269 claiming benefit of U.S. Appl. No. 13/447,372, filed Apr. 12, 2013 with English translation.
International Preliminary Report on Patentability dated Oct. 27, 2016 for Application No. PCT/US2015/025867 filed Apr. 15, 2015.
International Search Report and Written Opinion dated Jan. 3, 2017 for PCT/US2016/049464 claiming benefit of U.S. Appl. No. 14/840,217, filed Aug. 31, 2015.
International Search Report and Written Opinion dated Oct. 22, 2015 corresponding to PCT/US2015/025867 filed Apr. 15, 2015.
Extended European Search Report dated Jul. 3, 2017 in corresponding European Application No. 17151461.5.
European Office Action dated Jul. 27, 2017 in corresponding European Application No. 14747254.2.
International Preliminary Report on Patentability dated Oct. 12, 2017 in corresponding/related International Application No. PCT/US2016/023349.
Canadian Office Action dated Aug. 22, 2017 in corresponding/related Canadian Application No. 2,945,806.

\* cited by examiner

SURGICAL BURS WITH GEOMETRIES HAVING NON-DRIFTING AND SOFT TISSUE PROTECTIVE CHARACTERISTICS

FIELD

The disclosure relates to a surgical systems for bone cutting or shaping, and more particularly to surgical burs.

BACKGROUND

This section provides background information related to the present disclosure which is not necessarily prior art.

Surgical burs need sharp and durable cutting edges in order to efficiently dissect, cut and/or shape bone during a surgical procedure. Human anatomy tends to locate sensitive soft tissue structures, such as nerves and blood vessels, near bones for protection. These structures can include the dura mater. Dura mater (or dura) refers to the outermost layer of protective soft tissue surrounding the brain and spinal column of a patient. During cranial and spinal procedures, the distal end of a bur can come in contact with dura mater. The term "distal" means furthest away from a medical practitioner holding a surgical tool with a rotating bur. The term "proximal" means towards the medical practitioner and away from the patient.

Damage to the dura mater can increase risks of infections (e.g., meningitis) and/or result in surgical complications (e.g., swelling of the brain). Thus, in order to preserve the integrity of the dura mater, it is desirable for surgical burs, intended for dissection of bone, to have a high-level of control (minimal flail or chatter) and have a geometry not predisposed to dissect soft tissue.

SUMMARY

This section provides a general summary of the disclosure, and is not a comprehensive disclosure of its full scope or all of its features.

A surgical bur is provided and includes a body and a drill point. The body includes flutes and lands. Each of the flutes includes a cutting edge, a rake face, and a clearance surface. Each of the lands is convex-shaped and disposed between a pair of the flutes. The drill point includes axial relief surfaces. Each of the axial relief surfaces has a planar area, is distinct from the lands and borders (i) a distal portion of one of the cutting edges, (ii) one of the lands, and (iii) one of the clearance surfaces.

In other features, a surgical bur is provided and includes a body and a drill point. The body includes flutes and lands. Each of the flutes includes a cutting edge and a clearance surface. Each of the lands is disposed between a pair of the flutes. The drill point includes axial relief surfaces. Each of the axial relief surfaces is distinct from the lands and borders (i) a distal portion of one of the cutting edges, (ii) one of the lands, and (iii) one of the clearance surfaces. At least one axial relief angle of the axial relief surfaces is within a predetermined range.

In other features, a surgical bur is provided and includes a body and a drill point. The body includes flutes and lands. Each of the flutes includes a cutting edge and a clearance surface. Each of the lands is disposed between a pair of the flutes. The drill point includes axial relief surfaces. Each of the axial relief surfaces is distinct from the lands and borders (i) a distal portion of one of the cutting edges, (ii) one of the lands, and (iii) one of the clearance surfaces. The drill point has a drill point angle of greater than or equal to a predetermined angle.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Drill bits for machining naturally occurring and/or engineered materials, such as metal, wood and plastic have drill point geometries for improved cutting efficiency, stability, and feed rates, as well as for minimized thermal energy build-up during machining. In general, drill point angles for machining softer materials are more acute than those for machining harder materials.

Figure 1:
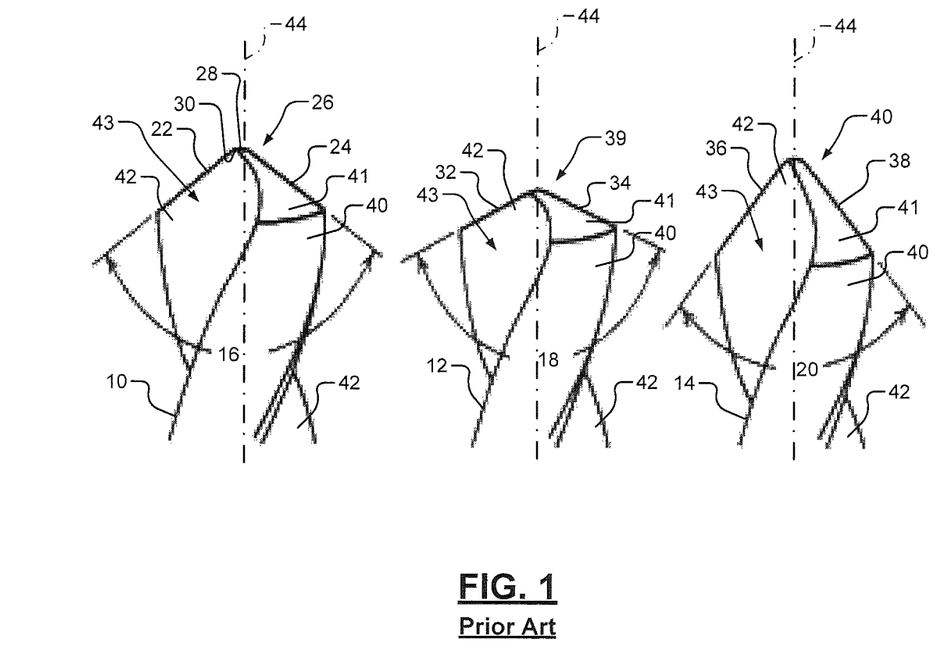
FIG. 1 is a side perspective view of three drill bits illustrating drill point angles.

FIG. 1 shows side views of three drill bits 10, 12, 14 and corresponding drill point angles 16, 18, 20. A drill point angle refers to an angle between tip cutting edges (e.g., tip cutting edges 22, 24) of a tip (e.g., tip 26) of a drill bit. The tip cutting edges extend radially away from (i) a center (e.g., center 28) of the tip, and (ii) respective ends of a chisel edge (e.g., chisel edge 30) of the drill bit.

The drill bits 10, 12, 14 are shaped to work on materials having different hardness characteristics. The drill point angle 16 of the first drill bit 10 may be, for example, 118° and is for materials having a first hardness. The first drill bit 10 has the tip cutting edges 22, 24. The drill point angle 18 of the second drill bit 12 may be, for example, 135° and is for materials having a second hardness. The second hardness is greater than the first hardness. The second drill bit 12 has tip cutting edges 32, 34. The drill point angle 20 of the third drill bit 14 may be, for example, 90° and is for materials have a third hardness. The third hardness is less than the second hardness and the first hardness. The third drill bit 14 has tip cutting edges 36, 38.

The drill bits 10, 12, 14 have respective tips 26, 39, 40. Each of the tips 26, 39, 40 includes relief surfaces that extend away from the respective cutting edges 22, 24, 32, 34, 36, 38. Although the relief surfaces are distinct surfaces, the relief surfaces are identified by numerical designator 41. The relief surfaces 41 are convex-shaped.

Each of the drill bits 10, 12, 14 has two helically shaped lands and two flutes. Although the lands are distinct surfaces, the lands are identified by numerical designator 40. Although the flutes are distinct from each other, the flutes are identified by numerical designator 42. The lands 40 are not convex-shaped. Each of the flutes 42 is located between a pair of the lands 40 and has a corresponding chip space 43 along and in the flutes. The lands 40 are in respective 180° locations about a corresponding longitudinal axis (the longitudinal axes are identified by numerical designator 44). The flutes 42 are also in respective 180° locations about a corresponding longitudinal axis.

Figure 2:
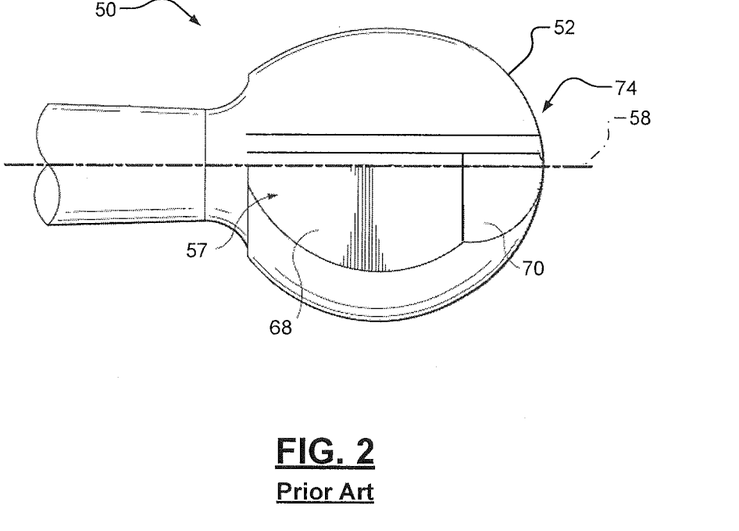
FIG. 2 is a side view of a dissection tool.
Figure 3:
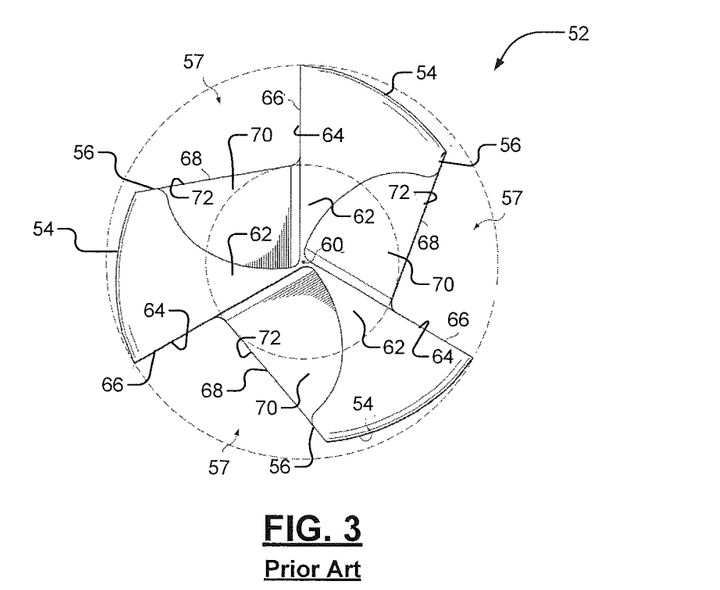
FIG. 3 is an end view of the dissection tool of FIG. 2.

FIG. 2-3 show side and distal end views of a predicate dissection tool 50 including a surgical bur 52. The surgical bur 52 includes three cam shaped lands 54 and three flutes 56. Each of the flutes 56 is located between a pair of the lands 54 and has a corresponding chip space 57. The lands 54 are equally spaced about a longitudinal axis 58 of the surgical bur 52. The longitudinal axis 58 is shown by point 60 in FIG. 2. Distal portions 62 of the lands 54 are referred to as axial relief surfaces 63, which are convex-shaped. The axial relief surfaces 62 are not distinct from the lands 54 because: the lands 54 and the axial relief surfaces 62 are both convex-shaped (or have the same type of surface); and the axial relief surfaces 62 are continuous with the lands 54 without transitional surfaces or borders between the axial relief surfaces 62 and the lands 54.

The flutes 56 are also equally spaced about the longitudinal axis 58. Each of the flutes 56 has a rake face 64 with a cutting edge 66 and a clearance surface 68. Each of the clearance surfaces 68 includes distal portion (or surface) and a proximal portion (or surface). The distal portions of the clearance surfaces 68 are identified by numerical designator 70. The proximal portions of the clearance surfaces 68 are identified by numerical designator 72.

The geometries of the drill bits 10, 12, 14 of FIG. 1 and the surgical bur 52 of FIGS. 2-3 have associated disadvantages. Although the drill bits 10, 12, 14 provide cutting efficiency and stability due to the corresponding drill point angles, the geometries of the drill bits 10, 12, 14 would be inappropriate for surgical use in certain procedures. This is because the drill bits would likely cut dura mater and can be difficult to use for shaping purposes. The tips 26, 39, 40 of the drill bits 10, 12, 14 have a minimal amount of contact surface area, which increases chances of cutting dura mater. Although the surgical bur 52 is rounded and has a less tendency to cut dura mater than the drill bits 10, 12, 14, the surgical bur 52 has an increased tendency to drift due to the geometries of a distal end or tip 74 of the surgical bur 52. The surgical bur 52 also has a greater amount of contact area, requiring more irrigation to mitigate friction and the concomitant torsional shear forces that may be exerted on an underlying soft tissue structure. For at least these reasons, it is desirable to construct surgical burs (or drilling tools) with geometries including a rounded tip and certain rake, axial relief and drill point angles, such that the surgical burs do not engage soft tissue and/or dura mater.

The following description discloses rotatable surgical burs (referred to below as the surgical burs). The surgical burs have fewer tendencies to cut dura mater and increased tendency to cut bone more efficiently as compared to predicate burs due to the geometries of the surgical burs. The surgical burs also have fewer tendencies to drift into sensitive anatomy. The surgical burs have tips with distal geometries that allow the surgical burs, with adequate irrigation, to glide over the dura mater without engaging and/or tearing the dura mater. The distal geometries include: axial relief surfaces with planar shapes and increased surface area; drill point angles in predetermined ranges; and axial relief angles in predetermined ranges. The distal geometries are set for maximum cutting and stability performance and for minimal tendencies to engage dura mater. The gliding aspect occurs over dura mater as opposed to bone due to the soft flexible nature of dura mater and the balance of surface area, shapes, and angles of the axial relief surfaces. The surgical burs have an increased tendency to cut into bone where the surgical burs are placed without drifting into nearby anatomy.

Although the surgical burs disclosed herein may be used, for example, for cutting and shaping bone, the surgical burs may be used for other dissecting, cutting, and/or shaping purposes. The disclosed implementations include bur configurations that minimize risk for challenges to sensitive anatomy, in particular, dura mater. The surgical burs are constructed with geometry to allow a practitioner to perform a procedure (e.g., a craniotomy) including casual contact atop dura mater. The surgical burs allow the practitioner to create a bore through a bone and/or a lateral path in the bone without tearing dura mater.

Example embodiments will now be described more fully with reference to the accompanying drawings. The following description is merely exemplary in nature and is not intended to limit the present disclosure, application, or uses. It should be understood that throughout the drawings, corresponding reference numerals indicate like or corresponding parts and features.

Figure 4:
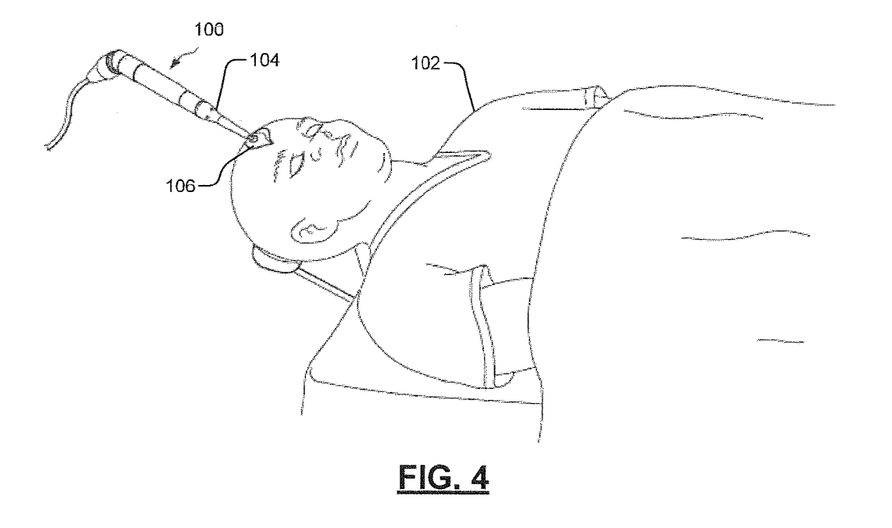
FIG. 4 is a perspective view of a surgical dissection cutter assembly incorporating a bur and in use on a patient in accordance with an embodiment of the present disclosure.

FIG. 4 shows a surgical dissection cutter assembly 100 incorporating a rotating surgical bur in use on a patient 102. The patient is undergoing a neurological operation. Access to the brain or other neurological structures often requires delicate dissection of bone and other tissues. FIG. 4 is provided for example purposes only, the surgical burs disclosed herein may be used in different tools and/or cutter assemblies and may be used for other procedures and/or operations. The dissection cutter assembly 100 includes a dissection tool driver 104, which is being utilized to dissect a portion of bone and adjacent tissue of the patient 102 in the surgical access site 106.

Figure 5:
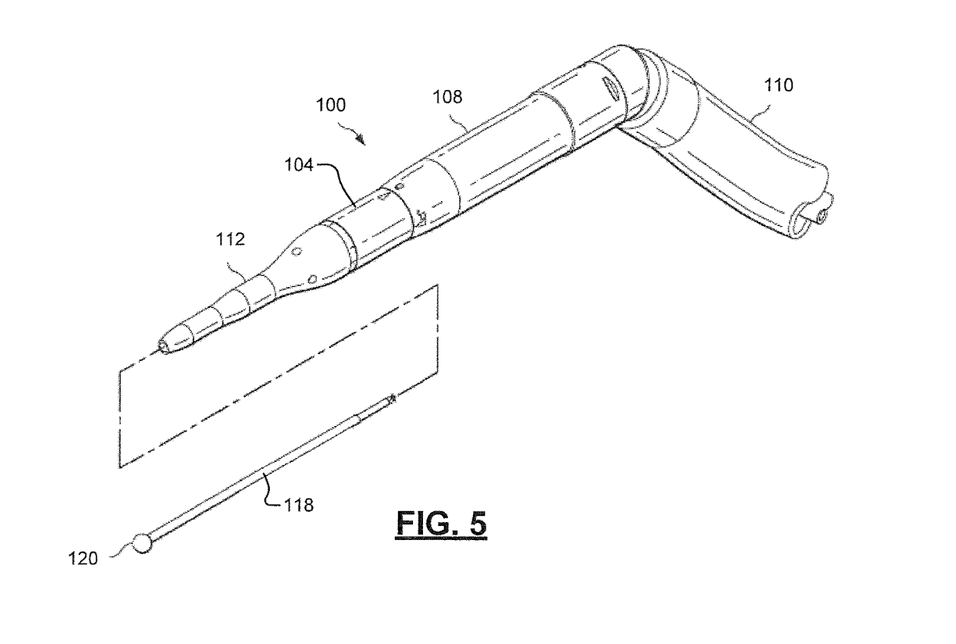
FIG. 5 is a perspective view of the surgical dissection cutter assembly of FIG. 4.

FIG. 5 is a perspective view of the surgical dissection cutter assembly 100. The dissection tool driver 104 includes a motor housing 108 connected to a hose or cable assembly 110. The hose assembly 110 supplies external power and control for the motor housing 108. The dissection tool driver 104 further includes an attachment housing 112 that connects to a dissection tool 118. A distal end of the dissection tool 118 includes a surgical bur 120. Examples of the dissection tool 118 are shown and described below with reference to FIGS. 6-13.

Figure 6:
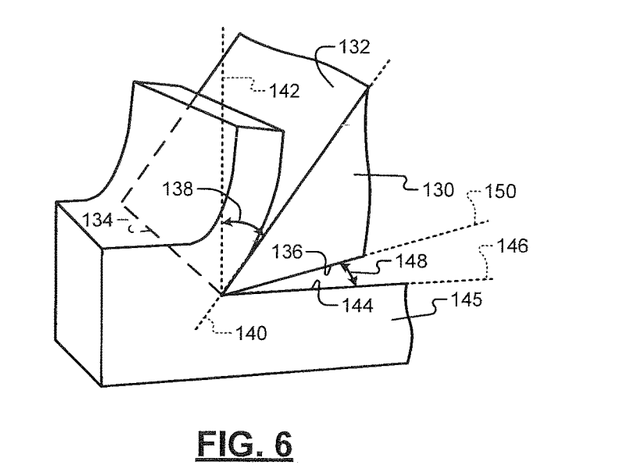
FIG. 6 is a perspective view of a portion of a surgical bur illustrating a rake angle and a relief angle in accordance with an embodiment of the present disclosure.

FIG. 6 is a perspective view of a portion 130 of a surgical bur. The portion 130 includes a rake face 132 with a cutting edge 134 and a relief surface 136. The cutting edge 134 may be at a distal end of the surgical bur and adjacent to the axial relief surface 136. A rake angle 138 of the rake face 132 may be between (i) a line (or plane) 140 on the rake face 132 and a plane perpendicular to the cutting edge 134 and (ii) a line (or plane) 142 extending perpendicular to a surface 144 of a bone 145 into which the surgical bur is cutting and extending in a direction of the cut and/or a line (or plane) 146 perpendicular to line 142. An axial relief angle 148 may be between (i) a line (or plane) 150 on the axial relief surface 136 and a plane perpendicular to the cutting edge 134 and (ii) the line 146.

Although the following surgical burs are shown as having a particular number of flutes, lands, axial relief surfaces, clearance surfaces, etc., the surgical burs may have other quantities of each of these items.

Figure 7:
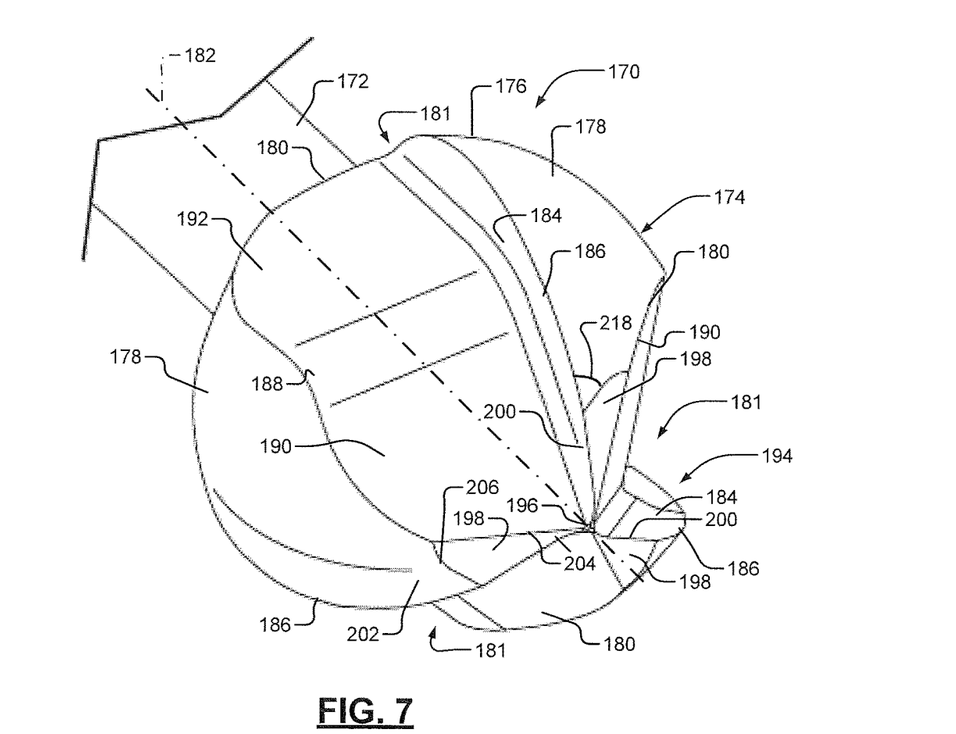
FIG. 7 is a perspective view of a dissection tool including a surgical bur in accordance with an embodiment of the present disclosure.

FIG. 7 is a perspective view of a dissection tool 170. The dissection tool 170 includes a shaft 172 and a surgical bur 174. The surgical bur 174 includes a body 176. The body 176 has three cam shaped lands 178 and three flutes 180. Each of the flutes 180 is located between a pair of the lands 178 and has a corresponding chip space 181. The lands 178 are convex-shaped and/or rounded and may be in respective 120° locations about a longitudinal axis 182 of the dissection tool 170, the shaft 172, and/or the surgical bur 174. The flutes 180 may also be in respective 120° locations about the longitudinal axis 182. Each of the flutes 180 has a rake face 184 with a cutting edge 186 and a clearance surface 188. Each of the clearance surfaces 188 includes a distal portion (or surface) 190 and a proximal portion (or surface) 192.

The surgical bur 174 includes a drill point 194 at a distal end of the surgical bur 174. The drill point 194 may include a center point 196 and three axial relief surfaces 198. The longitudinal axis 182 passes through the center point 196. The axial relief surfaces 198 are at ends of the flutes 180 and are distinct from the lands 178. The axial relief surfaces 198 are distinct from the lands 178 because: the axial relief surfaces 198 are a different type of surface than the lands (e.g., the lands 178 may be convex-shaped and the axial relief surfaces 198 may be planar shaped); there are transitional surfaces (or borders) between the axial relief surfaces 198 and the lands 178; and/or the axial relief surfaces 198 do provide a non-transitional (or continuous surface) with the lands.

Each of the axial relief surfaces 198 are bordered by (i) a respective distal end portion 200 of one of the cutting edges 186, (ii) a distal end portion 202 of one of the lands 178, and (iii) one of the distal portions 190 of one of the clearance surfaces 188. The axial relief surfaces 198 may be flat (or planar) surfaces, as shown. Each of the axial relief surfaces 198 are triangular-shaped with two nominally straight edges (two of the nominally straight edges are identified by numerical designator 204) and a curved edge (one of the curved edges is identified by numerical designator 206). The curved edges 206 of the axial relief surfaces 198 border respectively the lands 178.

Figure 8:
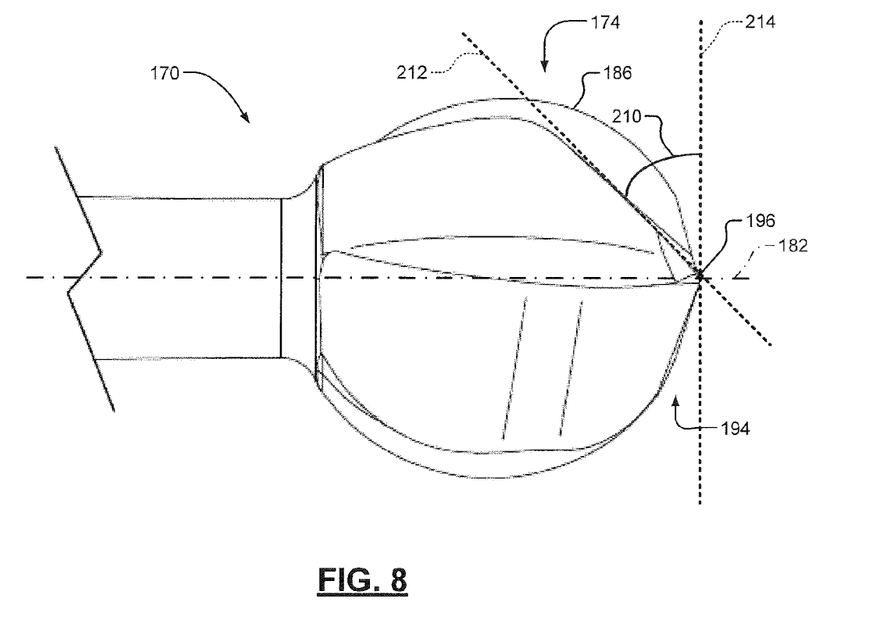
FIG. 8 is a side view of the dissection tool of FIG. 7.

FIG. 8 shows another side view of the dissection tool 170 including the surgical bur 174 is shown. The surgical bur 174 includes the cutting edges 186. The cutting edges 186 may provide a right-hand helix, straight or left-hand helix with respect to the longitudinal axis 182. The cutting edges 186 are shown as providing a right-hand helix. When viewed from the side and as shown, the cutting edges 186 of the right-hand helix configuration extend along the longitudinal axis 182, generally from above to below the, and towards the drill point 194. When viewed from the side, the cutting edges 186 of the straight configuration extend towards the drill point 194 and parallel with the longitudinal axis 182. When viewed from the side, the cutting edges 186 of the left-hand helix configuration extend along the longitudinal axis 182, generally from below to above, and towards the drill point 194.

The surgical bur 174 also includes the clearance surfaces 188 having the distal surfaces 190. The distal surfaces 190 have corresponding gash angles (one gash angle 210 is shown). Each of the gash angles refers to an angle between (i) a line (or plane) 212 extending parallel to one of the distal surfaces 190 and away from the center point 196 and/or the longitudinal axis 182 and (ii) a line (or plane) 214 extending perpendicular to the longitudinal axis 182.

Figure 9:
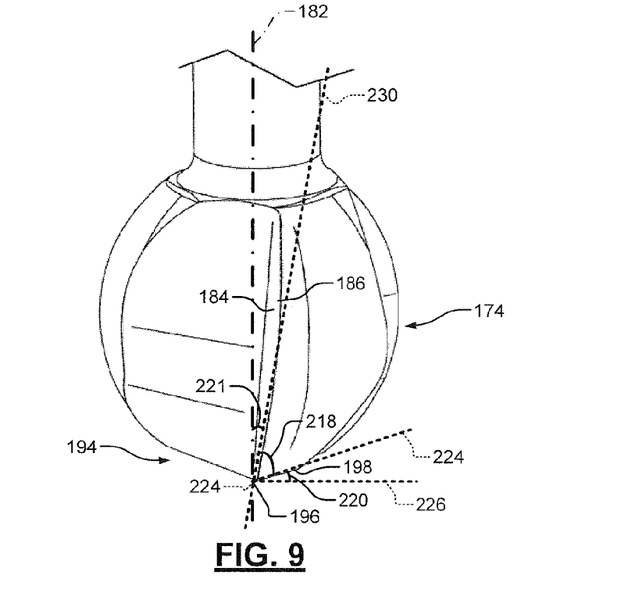
FIG. 9 is a side view of the surgical bur of FIG. 7 orthogonal to the distal end portion of one of multiple cutting edges of the surgical bur.

FIG. 9 shows another side view of the surgical bur 174 orthogonal to the distal end portion 200 of one of the cutting edges 186. The surgical bur 174 includes the axial relief surfaces 198 (one is shown in FIG. 9) and the rake faces 184 (one is shown in FIG. 9) with corresponding cutting edges 186 therebetween.

Each of the axial relief surfaces 198 has a corresponding axial relief angle (one axial relief angle 220 is shown) and axial rake angle (one axial rake angle 221 is shown). Each axial relief angle 220 can be measured between (i) a first line (or plane) 224 on an axial relief surface and observed perpendicular to the distal end portion 200 of one of the cutting edges 186 and (ii) a second line (or plane) 226 perpendicular to the longitudinal axis 182. The second plane 226 may also extend across a surface of an object (e.g., a surface of a bone) being cut. Each axial rake angle refers to an angle between (i) a third line (or plane) 230 on one of the rake faces 184 and observed perpendicular to the distal end portion 200 of one of the cutting edges 186 and (ii) a fourth line (or plane) extending along, passing through, and/or parallel to the longitudinal axis 182.

Each distal portion 222 of the cutting edges 186, along a corresponding one of the axial relief surfaces 198, has a corresponding axial relief surface angle, a drill point angle, and a remainder angle. The axial relief surface angle (e.g., axial relief surface angle 220) refers to an angle between (i) a line (or plane) 224 extending along and parallel to one of the axial relief surfaces 198 and away from the longitudinal axis 182 and/or distal portion 222 of one of the cutting edges 186, and (ii) a line (or plane) 226 extending perpendicular to the longitudinal axis 182 and passing through the center point 196.

A remainder angle (e.g., remainder angle 218) may refer to an angle between (i) a line (or plane) 230 on one of the rake faces 184 and observed perpendicular to the distal end portion 200 of one of the cutting edges 186 and (ii) the line (or plane) 224 extending along and parallel to one of the axial relief surfaces 198 and away from the longitudinal axis 182 and/or the distal portion 222 of one of the cutting edges 186. The remainder angle 218 is shown in FIGS. 7 and 9. The remainder angle 218 may be an acute, right, or obtuse angle. In one implementation, the remainder angle 218 is an obtuse angle.

Figure 10:
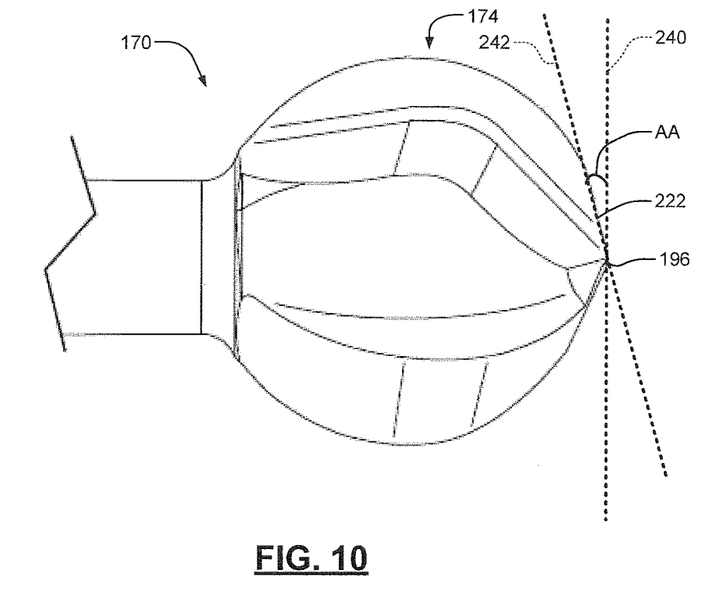
FIG. 10 is another side view of the dissection tool of FIG. 7.
Figure 13:
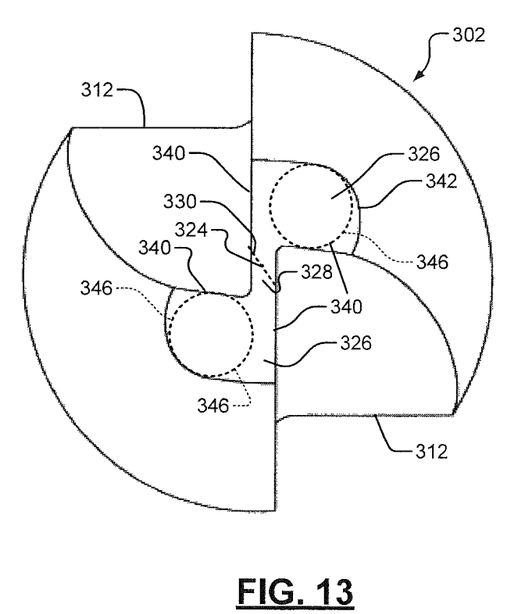
FIG. 13 is a distal end view of the dissection tool of FIG. 12.
Figure 14:
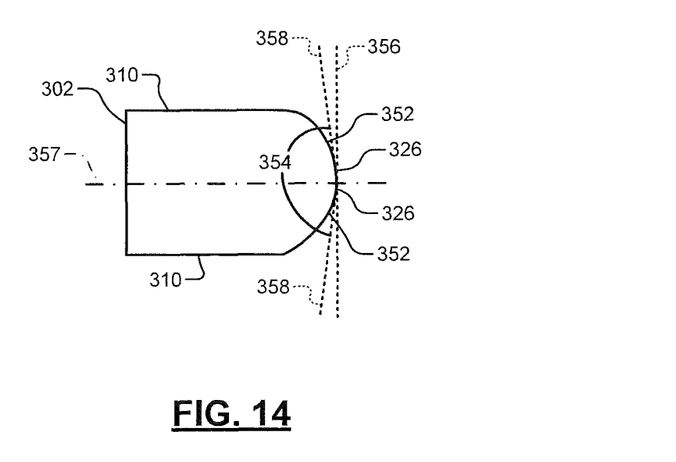
FIG. 14 is a side view of the surgical bur of FIG. 12 illustrating a drill point angle.

A drill point angle is described with respect to FIG. 10 and an example drill point angle is shown in FIG. 14. FIG. 10 shows a side view of the dissection tool 170 including the surgical bur 174 is shown. Multiple techniques may be used to determine the drill point angle. A drill point angle DP (not shown in FIG. 9) may be equal to 180° minus two times an acute angle (AA) (or DP=180°−2AA). The acute angle AA refers to an angle between (i) a line (or plane) 240 extending perpendicular to the longitudinal axis and tangent to the center point 196 and (ii) a line (or plane) 242 extending parallel to the distal portion 222 of one of the cutting edges 186. When a surgical bur has two flutes and/or opposing cutting edges with distal portions 180° apart and extending away from a center point, a corresponding drill point angle of the surgical bur refers to an angle between distal portions of the cutting edges. An example surgical bur with two flutes is shown in FIGS. 12-13.

Figure 11:
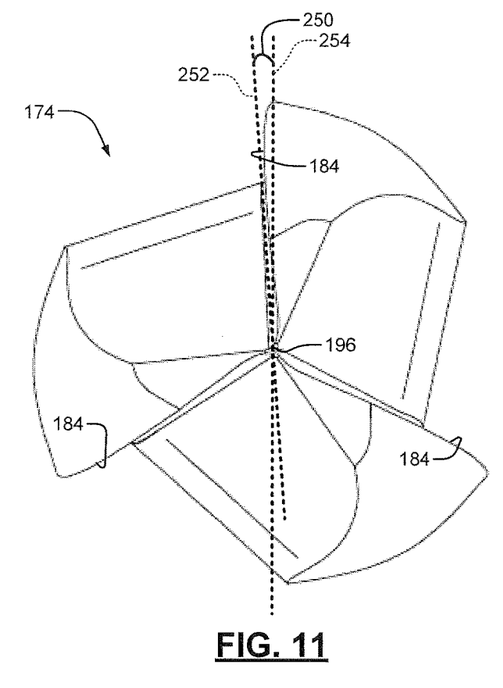
FIG. 11 is a distal end view of the surgical bur of FIG. 7.

FIG. 11 shows a distal end view of the surgical bur 174. The surgical bur 174 includes the rake faces 184. Each of the rake faces 184 has a corresponding radial rake angle 250. A radial rake angle 250 refers to an angle between (i) a line (or plane) 252 parallel to a rake face and (ii) a line (or plane) 254 passing through the cutting edge 186 and the longitudinal axis. Radial rake angles 250 of the rake faces 184 may be associated with a left-hand helix, straight or righted-hand helix with respect to the longitudinal axis 182 (shown in previous FIGS. 7-9). The rake faces 184 of the surgical bur 174 as shown provide a right-hand helix.

Figure 12:
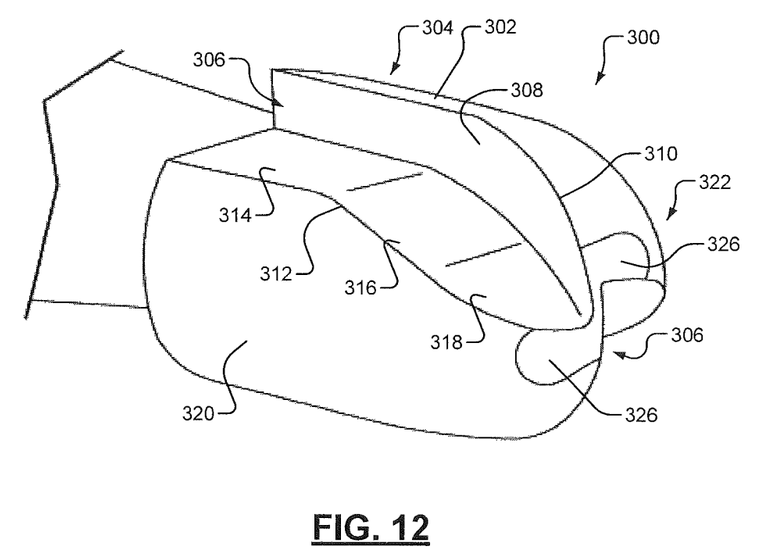
FIG. 12 is a perspective view of another dissection tool having a surgical bur in accordance with another embodiment of the present disclosure.

FIGS. 12 and 13 show perspective and distal end views of another dissection tool 300 having a surgical bur 302. The surgical bur 302 as shown has a straight configuration. The surgical bur 302 has a body 304 with two flutes 306 equally spaced around longitudinal axis 357.

Each of the flutes 306 has a rake face 308 with a cutting edge 310 and a clearance surface 312. Each clearance surface 312 may include a proximal portion (or surface) 314, a center portion (or surface) 316, and a distal portion (or surface) 318. A land 320 exists between each cutting edge 310 and a corresponding clearance surface 312. The lands 320 are convex-shaped.

The surgical bur 302 also includes a drill point 322 with a center point 324 and axial relief surfaces 326. The axial relief surfaces 326 may be flat (or planar) surfaces. A bridge 328 may extend between the axial relief surfaces 326 and/or be part of the axial relief surfaces 326. The bridge 328 may extend across the center point 324 and have a corresponding thickness and/or a chisel edge 330. In one implementation, the bridge 328 does not include a chisel edge. The chisel edge 330 may extend across the bridge 328 between the flutes 306. Each of the axial relief surfaces 326 includes two straight edges 340 and a curved edge 342. The curved edges 342 border respectively the lands 320. Each of the axial relief surfaces 326 may include circular areas 346. In one implementation, the circular areas 346 are flat (or planar), protrude from the remainder of the axial relief surfaces 326, and do not protrude from (or in a more distal direction than) the bridge 328. In another implementation, the axial relief surfaces 326 do not include the circular areas 346.

The rake faces 308: extend parallel to each other; are not in alignment with each other; are offset from each other; and have overlapping portions (i.e. the portions are side-by-side) at the bridge 328. Similarly, the straight edges 340: extend parallel to each other; are not in alignment with each other; are offset from each other; and have overlapping portions (i.e. the portions are side-by-side) at the bridge 328.

FIG. 14 shows a side view of the surgical bur 302. The surgical bur 302 includes the cutting edges 310 and axial relief surfaces 326. The distal portions 352 of the cutting edges 310 have an associated drill point angle 354. The drill point angle 354 is an obtuse angle. Acute angles between (i) distal portions 352 and (ii) a line (or plane) 356. A sum of the drill point angle 354 and the acute angles 356, 358 is equal to 180°. The plane 356 is perpendicular to a longitudinal axis 357 of the surgical bur 302. Lines (or planes) 358 tangent to the axial relief surfaces 326 are shown.

The above-disclosed implementations include surgical bur configurations designed to cut and shape bone efficiently while allowing contact with sensitive soft tissue structures (e.g., nerves, blood vessels, membranes, etc.) without tearing the soft tissue structures. This is especially applicable in neurological and spinal procedures where the dura mater can be exposed to a distal portion of a bur.

In certain implementations, drill point angles of surgical burs (e.g., the surgical burs 174 and 302) are obtuse angles greater than or equal to a first predetermined angle (e.g., 140°) and/or are within a first predetermined range (e.g., between 140°-160°). Corresponding axial relief angles of the surgical burs are less than or equal to a second predetermined angle (e.g., 25°) and/or are within a second predetermined range (e.g., between 5°-25°. An example drill point angle is shown in FIG. 14. An example axial relief angles are shown in FIGS. 6 and 9. These drill point angles and axial relief angles provide stable cutting of hard surfaces (such as surfaces of bone) while allowing the surgical burs to glide over soft surfaces (e.g., surfaces of dura mater). This is further improved by having the axial relief surfaces be planar surfaces. Rake angles of the surgical burs may also be within predetermined ranges and based on the application of use.

As a result, "skating" over hard surfaces is prevented providing improved and consistent drilling control while not challenging (or negatively affecting) integrity of dura mater. Reduced skating improves cutting quality while reducing risk of surgical complications concomitant with dural tears. The geometry of the surgical burs including the drill point angles and axial relief angles are tunable (i.e. can be adjusted) based on the application of use.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A surgical bur comprising:
    a body that is spherically-shaped, wherein the body comprises
        a plurality of flutes, wherein each of the plurality of flutes comprises a cutting edge, a rake face and a clearance surface, and
        a plurality of lands, each of the plurality of lands is convex-shaped and disposed between a pair of the plurality of flutes; and a drill point comprising a plurality of axial relief surfaces, wherein each of the plurality of axial relief surfaces has a planar area, is distinct from the plurality of lands and borders (i) a distal portion of one of the cutting edges, (ii) one of the plurality of lands, and (iii) one of the clearance surfaces;

wherein widths of the plurality of axial relief surfaces narrow towards a distal end of the drill point; and wherein lengths of proximal most edges of the plurality of axial relief surfaces are equal to lengths of distal most edges of the plurality of lands.

2. The surgical bur of claim 1, wherein drill point angles of distal portions of the cutting edges are each between 140°-160°.

3. The surgical bur of claim 1, wherein axial relief angles of the plurality of axial relief surfaces are each between 5°-25°.

4. The surgical bur of claim 1, wherein the plurality of axial relief surfaces are planar surfaces and meet at a center point.

5. The surgical bur of claim 4, wherein:
entire areas of the plurality of axial relief surfaces are respectively between the plurality of lands and the center point; and
the plurality of axial relief surfaces separate the plurality of lands from the center point.

6. The surgical bur of claim 1, wherein:
drill point angles of distal portions of the cutting edges are each between 140°-160°; and
axial relief angles of the plurality of axial relief surfaces are each between 5°-25°.

7. The surgical bur of claim 1, wherein:
the plurality of axial relief surfaces are triangular-shaped and comprise two straight edges and a curved edge; and
each of the curved edges of the plurality of axial relief surfaces border a respective one of the plurality of lands.

8. The surgical bur of claim 1, wherein the planar areas are circular in shape.

9. The surgical bur of claim 1, wherein:
at least one axial relief angle of the plurality of axial relief surfaces is less than or equal to a predetermined angle such that the surgical bur while rotating has a tendency to cut a first type of surface and not a second type of surface;
the first type of surface has a first hardness; and
the second type of surface has a second hardness that is less than the first hardness.

10. The surgical bur of claim 1, wherein:
the plurality of flutes are non-opposing flutes; and
the plurality of axial relief surfaces are connected via a bridge.

11. The surgical bur of claim 1, wherein each of the plurality of lands is convex-shaped along a longitudinal center axis of the surgical bur and from a proximal end of the body to a corresponding one of the plurality of axial relief surfaces.

12. The surgical bur of claim 11, wherein each of the plurality of lands is convex-shaped in a lateral direction between adjacent ones of the plurality of flutes.

13. The surgical bur of claim 1, wherein each of the cutting edges extend along a longitudinal center axis of the surgical bur from a proximal end of the surgical bur to a distal end of the surgical bur.

14. The surgical bur of claim 1, wherein each of the cutting edges, in a distal portion of the surgical bur, abuts a respective one of the plurality of lands and a respective one of the plurality of axial relief surfaces.

15. The surgical bur of claim 1, wherein:
the plurality of axial relief surfaces are planar surfaces, meet at a center point at a distal end of the surgical bur, and are triangular-shaped;
each of the plurality of axial relief surfaces has three edges;
the first edges border respectively the plurality of lands;
the second edges border respectively the clearance surfaces; and
the third edges border respectively the cutting edges.

16. The surgical bur of claim 15, wherein:
each of the second edges of the plurality of axial relief surfaces extends along a respective one of the clearance surfaces; and
points of the plurality of axial relief surfaces between the second edges and the third edges meet at the center point.

17. The surgical bur of claim 1, wherein a proximal end of each of the plurality of axial relief surfaces that borders a respective one of the plurality of lands is at an acute remainder angle relative to a respective one of the cutting edges bordering the respective one of the plurality of lands.

18. The surgical bur of claim 1, wherein:
each of the plurality of axial relief surfaces is a single surface having a respective peripheral boundary;
each of the plurality of axial relief surfaces are void of a transitional edge within the corresponding peripheral boundary; and
a transitional edge refers to an edge between two distinct surfaces.

19. The surgical bur of claim 1, wherein:
each of the plurality of axial relief surfaces comprises three edges;
the cutting edges extend along the first edges of the plurality of axial relief surfaces;
the plurality of lands have distal edges that extend along the second edges of the plurality of axial relief surfaces; and
the clearance surfaces have distal edges that extend along the third edges of the plurality of axial relief surfaces.

20. The surgical bur of claim 1, wherein the rake faces are offset from each other, are not in alignment with each other; and have overlapping portions.

21. The surgical bur of claim 20, wherein:
the rake faces extend parallel to each other; and
the overlapping portions are side-by-side to provide a bridge between the planar areas.

22. The surgical bur of claim 1, wherein each of the plurality of axial relief surfaces is planar-shaped.

23. The surgical bur of claim 1, wherein each of the plurality of axial relief surfaces is distal to a respective one of the clearance surfaces.

24. The surgical bur of claim 1, wherein each of the plurality of axial relief surfaces is distal to a respective one of the plurality of lands.

25. The surgical bur of claim 1, wherein the plurality of axial relief surfaces, the clearance surfaces and the cutting edges meet at a distal center end point of the surgical bur.

26. A surgical bur comprising:
a body that is spherically-shaped, wherein the body comprises
a plurality of flutes, wherein each of the plurality of flutes comprises a cutting edge, a rake face, and a clearance surface, and a plurality of lands, each of the plurality of lands is disposed between a pair of the plurality of flutes; and
a drill point comprising a plurality of axial relief surfaces, wherein each of the plurality of axial relief surfaces is distinct from the plurality of lands and borders (i) a distal portion of one of the cutting edges, (ii) one of the plurality of lands, and (iii) one of the clearance surfaces, wherein a proximal most edge of each of the plurality of axial relief surfaces borders a distal most edge of a respective one of the plurality of lands;
wherein widths of the plurality of axial relief surfaces narrow towards a distal end of the drill point; and
wherein lengths of the proximal most edges of the plurality of axial relief surfaces are equal to lengths of the distal most edges of the plurality of lands.

27. The surgical bur of claim 26, wherein:
each of the plurality of lands is convex-shaped; and
the plurality of axial relief surfaces are planar surfaces.

28. The surgical bur of claim 26, wherein:
at least one axial relief angle of the plurality of axial relief surfaces is less than or equal to a predetermined angle such that the surgical bur while rotating has a tendency to cut a first type of surface and not a second type of surface;
the first type of surface has a first hardness; and
the second type of surface has a second hardness that is less than the first hardness.

29. The surgical bur of claim 26, wherein axial relief angles of the plurality of axial relief surfaces are each less than or equal to 25°.

30. The surgical bur of claim 26, wherein axial relief angles of the plurality of axial relief surfaces are each between 5°-25°.

31. The surgical bur of claim 26, wherein drill point angles of distal portions of the cutting edges are each between 140°-160°.

32. The surgical bur of claim 26, wherein the plurality of axial relief surfaces are planar surfaces.

33. The surgical bur of claim 26, wherein each axial relief surface of the surgical bur is distal to a respective one of the plurality of lands or a respective one of the clearance surfaces.

34. The surgical bur of claim 26, wherein each axial relief surface of the surgical bur is distal to a respective one of the plurality of lands and a respective one of the clearance surfaces.

35. The surgical bur of claim 26, wherein each of the proximal most edges of the axial relief surfaces extends laterally between a respective one of the clearance surfaces and a respective one of the rake faces.

36. A surgical bur comprising:
a body that is spherically-shaped, wherein the body comprises
a plurality of flutes, wherein each of the plurality of flutes comprises a cutting edge and a clearance surface, and
a plurality of lands, each of the plurality of lands is disposed between a pair of the plurality of flutes, wherein each of the cutting edges borders a respective one of the plurality of lands in a distal portion of the surgical bur; and
a drill point comprising a plurality of axial relief surfaces, wherein each of the plurality of axial relief surfaces is distinct from the plurality of lands and borders (i) a distal portion of one of the cutting edges, (ii) one of the plurality of lands, and (iii) one of the clearance surfaces, wherein the drill point has a drill point angle of greater than or equal to a predetermined angle, and wherein a proximal end of each of the plurality of axial relief surfaces that borders a respective one of the plurality of lands is at an acute remainder angle relative to a respective one of the cutting edges bordering the respective one of the plurality of lands.

37. The surgical bur of claim 36, wherein:
the drill point angle is within a predetermined range such that the surgical bur while rotating has a tendency to cut a first type of surface and not a second type of surface;
the first type of surface has a first hardness; and
the second type of surface has a second hardness that is less than the first hardness.

38. The surgical bur of claim 37, wherein drill point angles of distal portions of the cutting edges are each between 140°-160°.

39. The surgical bur of claim 36, wherein axial relief angles of the plurality of axial relief surfaces are each between 5°-25°.

40. The surgical bur of claim 36, wherein the plurality of axial relief surfaces are planar surfaces.

41. A surgical bur comprising:
a body comprising
a plurality of flutes, wherein each of the plurality of flutes comprises a cutting edge, a rake face and a clearance surface, and
a plurality of lands, wherein each of the plurality of lands is convex-shaped and disposed between a pair of the plurality of flutes; and
a drill point comprising a plurality of axial relief surfaces, wherein each of the plurality of axial relief surfaces has a planar area, is distinct from the plurality of lands and borders (i) a distal portion of one of the cutting edges, (ii) one of the plurality of lands, and (iii) one of the clearance surfaces,
wherein each of the plurality of lands comprises
a first portion convex-shaped in a lateral direction between the plurality of flutes and is not convex-shaped along a longitudinal axis of the surgical bur, and
a second portion convex-shaped in a lateral direction between the plurality of flutes and convex-shaped along the longitudinal axis of the surgical bur;
wherein a proximal end of each of the plurality of axial relief surfaces that borders a respective one of the plurality of lands is at an acute remainder angle relative to a respective one of the cutting edges bordering the respective one of the plurality of lands.

42. The surgical bur of claim 41, wherein each axial relief surface of the surgical bur is distal to a respective one of the plurality of lands or a respective one of the clearance surfaces.

43. The surgical bur of claim 41, wherein each axial relief surface of the surgical bur is distal to a respective one of the plurality of lands and a respective one of the clearance surfaces.

* * * * *

UNITED STATES PATENT AND TRADEMARK OFFICE
CERTIFICATE OF CORRECTION

PATENT NO. : 9,883,873 B2  
APPLICATION NO. : 13/944650  
DATED : February 6, 2018  
INVENTOR(S) : Kulas et al.

Page 1 of 1

It is certified that error appears in the above-identified patent and that said Letters Patent is hereby corrected as shown below:

On the Title Page

Page 2, Applicant Information: Delete "Louisville, CO" and insert --Fort Worth, TX-- therefore;

In the Specification

Column 3, Detailed Description, Line 28: Delete "FIG." and insert --FIGS.-- therefore;

Column 3, Detailed Description, Line 36: Delete "63," and insert --62,-- therefore; and Column 8, Detailed Description, Line 12: Delete "5°-25°." and insert --5°-25°).-- therefore.

Signed and Sealed this  
Eighth Day of May, 2018

Andrei Iancu  
*Director of the United States Patent and Trademark Office*